United States Patent
Horkel

(10) Patent No.: US 6,648,842 B2
(45) Date of Patent: Nov. 18, 2003

(54) DELIVERY PREPARATION AND FACILITATION DEVICE AND PREPARATORY GYMNASTICS

(76) Inventor: Wilhelm Horkel, Maximilianstr. 5, D - 82319 Starnberg (DE)

( * ) Notice: Subject to any disclaimer, the term of this patent is extended or adjusted under 35 U.S.C. 154(b) by 0 days.

(21) Appl. No.: 09/403,253

(22) PCT Filed: Apr. 15, 1998

(86) PCT No.: PCT/EP98/02193
§ 371 (c)(1),
(2), (4) Date: Oct. 15, 1999

(87) PCT Pub. No.: WO98/46298
PCT Pub. Date: Oct. 22, 1998

(65) Prior Publication Data
US 2002/0010441 A1 Jan. 24, 2002

(30) Foreign Application Priority Data
Apr. 15, 1997 (DE) .......................... 197 15 724

(51) Int. Cl.[7] ............................... A61H 19/00
(52) U.S. Cl. ............. 601/45; 604/99.02; 604/101.01; 606/119; 606/193
(58) Field of Search ............. 604/96.01, 97.01–97.03, 604/98.01, 99.01, 99.02, 99.04, 100.01, 103.07, 915–916, 101.05, 275, 279; 606/192–193, 119; 600/33, 38, 591, 115–116; 128/836, DIG. 23; 607/138

(56) References Cited

U.S. PATENT DOCUMENTS

| | | | |
|---|---|---|---|
| 2,610,626 A | * | 9/1952 | Edwards |
| 2,849,001 A | | 8/1958 | Oddo |
| 2,849,002 A | | 8/1958 | Oddo |
| 3,045,677 A | * | 7/1962 | Wallace |
| 3,480,017 A | | 11/1969 | Shute |
| 3,502,328 A | * | 3/1970 | Hamilton |
| 3,626,949 A | | 12/1971 | Shute |
| 4,167,938 A | * | 9/1979 | Remih ............ 482/113 |
| 4,753,238 A | * | 6/1988 | Gaiser |
| 4,832,691 A | | 5/1989 | Witzel |
| 5,147,377 A | * | 9/1992 | Sahota |
| 5,674,238 A | * | 10/1997 | Sample et al. |
| 5,733,230 A | * | 3/1998 | Sawchuck et al. |
| 5,947,991 A | * | 9/1999 | Cowan |

FOREIGN PATENT DOCUMENTS

| | | |
|---|---|---|
| DE | 38 00 744 | 1/1988 |
| DE | 38 03 727 | 2/1988 |
| FR | 592104 | 3/1924 |
| WO | 0 663 197 | 1/1994 |

* cited by examiner

Primary Examiner—Brian L. Casler
Assistant Examiner—LoAn H. Thanh
(74) Attorney, Agent, or Firm—Katten Muchin Zavis Rosenman

(57) ABSTRACT

A device for preparing a pregnant woman to delivery and facilitating the delivery itself, which comprises an entirely expandable stretch body, which is positioned in the expulsion area of the urogenital canal in such a way that it is partly inside the vagina and partly outside. There is also disclosed a preparatory gymnastics method involving the inventive device.

8 Claims, 3 Drawing Sheets

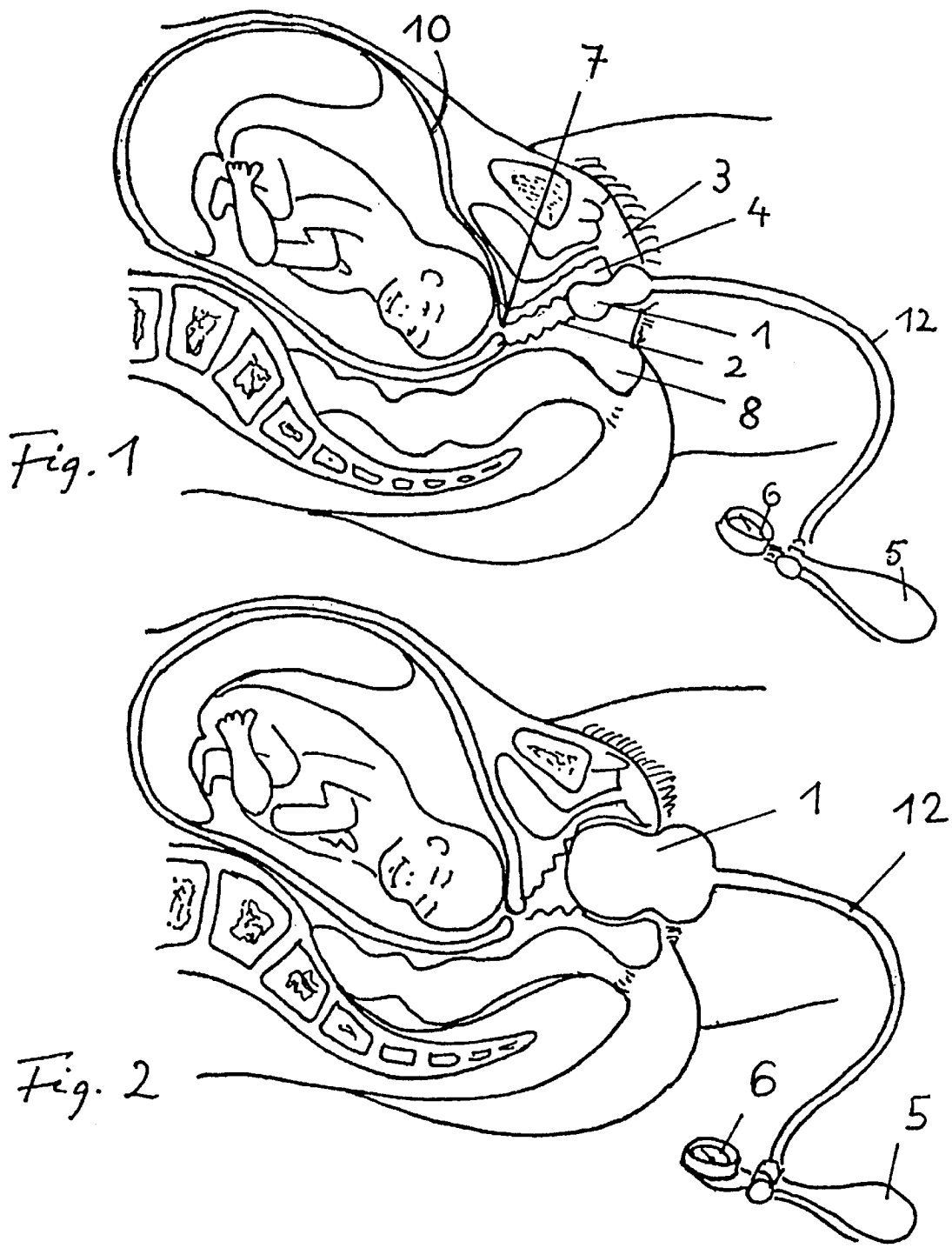

DELIVERY PREPARATION AND FACILITATION DEVICE AND PREPARATORY GYMNASTICS

The present invention relates to a device for helping a pregnant women to prepare for giving birth and to make giving birth easier which has an expandable elongated body which is positionable in the region of the vaginal orifice such that it is located partly inside the vagina and partly outside of the vagina. The invention further relates to an exercise method involving the use of such a device for preparing to give birth.

In Germany, there are approximately 850,000 births per year. According to the most recent available perinatal statistics of 1995, the rate of episiotomy, among both first time and subsequent births, was a total of 58.9% (less the rate of cesarean section of 17.4%). This means that approximately 500,650 epiosotomies are carried out yearly in Germany (Commission for Perinatalogy and Neonatalogy, BPE Annual Report 1995). In about 20% of all births a tear in the perineum occurs as a result of which the risk of death due to complications is further increased. In spite of numerous traditional and modem methods for preparing and for facilitating giving birth (e.g. Leboyer, Read, Odent), the mentioned statistics remain unchanged in relation to one another after decades. Even the new age pregnancy exercises to prepare for giving birth and the pregnancy consultation of midwives have only improved these figures unsubstantially.

The episiotomy, first described by Ould in 1742, still conjures up a horrible image even after 250 years. Although, it was proposed and carried out as a relief for women and to accelerate delivery, it is still feared by many women to this day due to its painfulness, and it is hated for its negative consequences. Avoidance of the episiotomy has therefore been a long felt need in the field along with the goal to make the delivery easier for mothers with less fear involved.

An additional problem of modem birthing assistance is the increasing disproportion between the fetal/infant head and the female pelvis. The cranial circumference of newborns is steadily increasing such that the measurement program established by Hausmann for the standard size of the biparietal diameter using ultrasound must be continuously upwardly corrected. The cause for this might be seen, on the one hand, to be the result of increasing exposure of pregnant women to light, noise, and other stimulation (for example neon lights, electro smog, car noise, etc . . . ), and on the other hand, due to the natural, modem androgenous type of woman (tall, narrow female pelvis and narrow hips) which naturally makes giving birth more difficult.

It is known for treating sedimentation of the blood and incontinence problems in women to insert an inflatable balloon deep into the vagina in order to provide, in the inflated state, a mechanical blockage of the bladder while raising the uterus. For example, European Patent publication EP 0,663,197 A1 describes a support body which keeps its shape and is made of elastic rubber material with areas of different wall thickness which expands conically from a base region in the direction of a top surface at the opposite end of the support body in a conical manner, a piece of hose being sealingly connected to the base region. The top surface is reinforced in a ring-shape and has a soft concavely formed inner region. The support body is inserted into the vagina with the base downward and is left in place for hours to support the vaginal wall.

U.S. Pat. No. 3,626.949 describes a cervical dilator which has not however achieved any significant success in practice. It discloses a PVC envelope or case having a hose connection for filling up the case with a fluid under pressure. The case can be inserted into the cervical canal while folded up and is then periodically expanded under pressure such that the case expands radially against the cervical wall to thereby simulate contractions. Between opposed ends of the case there is a waist portion which is not expandable in a radial direction, which waist portion is positioned inside the edge of the cervix in order to prevent that the expanded waist portion moves in an axial direction under pressure.

A further cervical dilator is described in U.S. Pat. No. 3,480,017. This dilator uses an inflatable case which is inflatable to a substantially disk-shaped body, which is positioned in use inside the uterus and inflatable using an inflation tube whose opening is inside the case. The case comprises a circumferential constriction such that a groove is formed in the cylindrical exterior wall of the case when inflated into a disk. The cervix supported by the groove can be expanded in this way in order to induce birth. The application of the known device is only possible by a doctor who has acquired the skills to manipulate the shell against the cervix using the inflating tube as a handle, without damaging the amniotic sack or the fetus' head. As a result of its flat disk shape, the known cervical dilator is particularly suited only for this application.

In French Patent publication FR-592,104, there is described a dilator to be inserted in the perineum which is made of an elongated elastic material balloon which can be laterally expanded by inflation while having its lengthwise expansion limited. By methodical use and progressive expansion, tissue having undergone such exercise will yield while giving birth without tearing.

This prior art balloon can also be actuated intermittently using a three-way valve. During use, it is important to pay attention that the balloon is only inserted into the vagina to the extend that the middle section of the balloon rests in the area of the perineum. During inflation, the balloon should form inside the perineum a ring-shaped constriction by means of which the balloon is secured in the axial direction.

In the embodiment of this prior art in which the balloon has a central inflation tube, there is the danger that the inner end of the tube is pushed during insertion too close to the cervix where serious injury is possible (causing bleeding or breakage of the amniotic sack).

In the case of the embodiment in which the balloon is provided with non-stretchable inner strips for preventing a lengthwise extension of the balloon, there is the danger that the balloon will be suddenly catapulted inwardly towards the cervix during inflation once a predetermined level of inflation is reached, which can lead to the above-mentioned serious injuries.

The known device should therefore only be used under the supervision of a physician, in particular because it is practically impossible for a pregnant woman, due to the corresponding size of her abdomen, to locate the correct axial position of the balloon.

Accordingly, it is the object of the present invention to construct the above-mentioned device such that its application for a pregnant women is pleasant and safe, and can be carried out easily by herself; and, finally such that its use should substantially contribute to the significant reduction of perineum tearing or episiotomies occuring during birth. Associated therewith, an undesired drop in the pelvic floor, and later occurrences of bladder incontinence and sexual disturbance as a result of physiological and psychosomatic complications occurring postpartum can be prevented.

This object is provided by a device having the characteristics of claim 6 as well as a method having the characteristics of claim 1.

The device according to the invention comprises an expandable elongated shaped body which is positionable in the region of the vaginal orifice such that it is located partway inside the vagina and partway outside the vagina. By the expansion of the elongated body, the vagina can be substantially expanded and the birth canal as well as the vaginal orifice can be expanded in advance to facilitate giving birth. With this training and stretching effect, eposiotomies as well as an undesirable drop in the pelvic floor can be avoided to a large extent along with complications associated therewith. The expandable body maintains its distance from the cervix which it should never contact in order avoid irritations.

By shaping the expandable elongated body such that the shape facilitates its positioning in the area of the vaginal orifice, the device is self-centering in the region of the vaginal orifice and self-anchoring. This can be achieved for example by shaping the body as a FIG. 8 in its lengthwise axis. It is essential that the expandable body is expandable in its entirety (i.e. the whole shape expands), since specifically the expansion in the area of the vaginal orifice is to be exercised.

In accordance with a preferred embodiment, it is provided that the body is expandable by means of a variable fluid filling system. The fluid can be for example a gel or an aqueous liquid which may be temperature controlled if need be, or the fluid may be a gas such as air. In particular cases, air pressure provided by blowing with the mouth may be used. Also preferably, the body may be formed as a balloon having a filling tube connected to an end which during use is oriented externally. Latex or a silicone product are examples of skin compatible materials which may be used.

According to a preferred embodiment, the balloon is assembled from two parts or half-shells which are connected together along a circurmferential seam. The circumferential seam is preferably positioned in the area of the waist portion. The half of the device positioned outside of the vagina has a greater wall strength than the half positioned inside. In this way, it is provided that the balloon is self-stabilized under high pressure and leads to a minimal rise in pressure for vaginal dilation.

In a further preferred embodiment, the device comprises an air pump with a manometer or pressure gauge connected to the filling hose of the balloon. The pump which may comprise a hand-pump can be used to pump up the expandable body in steps or stages up to a maximum pressure which may be about 160 mm Hg, measured using the pressure gauge.

The pressure gauge preferably comprises an air-release screw which is used to release the pressure at the end of the therapy or for relief during use.

Finally, it is important to make sure that the maximum expansion of the balloon transversely to the lengthwise axis measures 9 to 10 cm, preferably 9.4 to 9.6 cm. This corresponds approximately to the average diameter of a newborn head with a cranial circumference of approximately 35 cm at birth.

A further embodiment provides that a safety valve be arranged on the pressure gauge in order to limit the maximum pressure. The pressure may be limited, for example, to 200 mm Hg. The safety valve opens when the pressure limit is exceeded.

According to another preferred embodiment, the balloon assembled from two-half shells is constructed such that the half shelves form two gas-tight chambers separated from one another. In this way, they can be each indepently filled or deflated such that the balloon can be adjusted to the individual needs of the patient. The hose for inflating and deflating the half-shell positioned inside the vagina is provided to pass through the other half-shell. Both hoses exit at the end of the balloon directed outwardly. The device is particulary advantageous for patients who have already given birth and who have during the previous birth endured tearing of the perineum leading to painful scarring. For this purpose, the device can be pumped up alternatingly in pressure steps of 10 mm Hg in order to exert pressure on alternating sides of the vaginal orifice.

In a further preferred embodiment, the half shell positioned in the vagina is fillable by means of a separate inflation hose. The separate filling hose can either pass outside of the device or through the inside of the half-shell positioned outside of the vagina such that both tubes extend outwardly from the birth canal. Furthermore, according to a variant embodiment, the two hoses extend concentrically one inside the other.

Finally, it preferred that the device comprises a three-way valve for selecting the filling mode of the two half-shells. The two separated fillable half-shells can be filled together or individually inflated. The filling pressure is monitored for each corresponding filling mode using the pressure gauge. Also, the order for deflation can be selected using the three-way valve. When using concentrically extending hoses, a corresponding constructively built three-way valve can be provided.

In addition to the above-mentioned device, the invention further relates to a method for preparing to give birth using exercises in which the device according to the invention is used such that the expandable body is positioned partly outside and partly inside the vaginal orifice, and thereafter is expanded to a desired size and finally maintained in an expanded state for a predetermined time in its position. Preferably, the expansion of the device is increased with each repeated use in order to achieve an increasing preparatory expansion of the birth canal. The method carried out as a stretching or expansion exercise should be carried out several times per day as of the thirty-sixth week of pregnancy. Additionally, it is preferable that the expanded body be removed carefully in a direction of the vaginal orifice after a predetermined time period. The time period that the device should remain in the birth canal is between 10 to 20 minutes, preferably 15 minutes, in accordance with the subjective feeling of the patient: too much stretching tension indicates too high a pressure in the balloon. Relief is achieved by the step-wise actuation of the air pressure release screw.

The numerous advantages of the mentioned method are: an easier delivery resulting from prior stretching or expansion of the birth canal and the outer vaginal orifice; a faster delivery, in particular in the case of first time mothers; better oxygen supply to the child as a result of minimal pressure on the fetal cranium as it emerges; a reduction of labor-inducing medication, in particular in the case of first time mothers; a reduction in the pain of childbirth and minimal cramping caused by stretchable musculature; a clear reduction in the use of pain killers and local anesthesia; less risk of allergic shock due to local anesthesia; a reduction in the use of peridural and epidural anesthesia (spinal cord anesthesic); a significant reduction in the need to resort an episiotomy which is always painful for the mother (and therefore feared by her) and the inevitable stitches following the episisiotomy; as well as a quicker recovery of the vaginal musculature by sparing the musculus bulbo cavernosus, musculus bulbo spongiosus and the musculus sphincter ani since the incidence of macro and micro muscle tearing is reduced.

Further advantages resulting from a problem-free delivery are better care of the child by the mother, who can be more active and agile in the absence of an episiotomy, such that she can care for the child herself without feeling sick and injured. As a result of the reduction of pain achieved according to the invention, the production of prolactine is increased whereby lactation (breast feeding) is improved. It is furthermore important that the physiology, function and appearance of the vagina and vulva are maintained to a large extent, and thereby the mother's sex life after giving birth is not affected. A shorter recovery time in hospital and the possibility of home birth may also contribute to relief of medical insurance plans.

The invention will be better understood by way of the following detail description of a preferred embodiment with reference to the appended drawings in which:

FIG. 1 illustrates a preferred embodiment of the device according to the invention in use in the deflated state;

FIG. 2 illustrates the embodiment as shown in FIG. 1 in which the device is in the expanded state;

Figure 3:
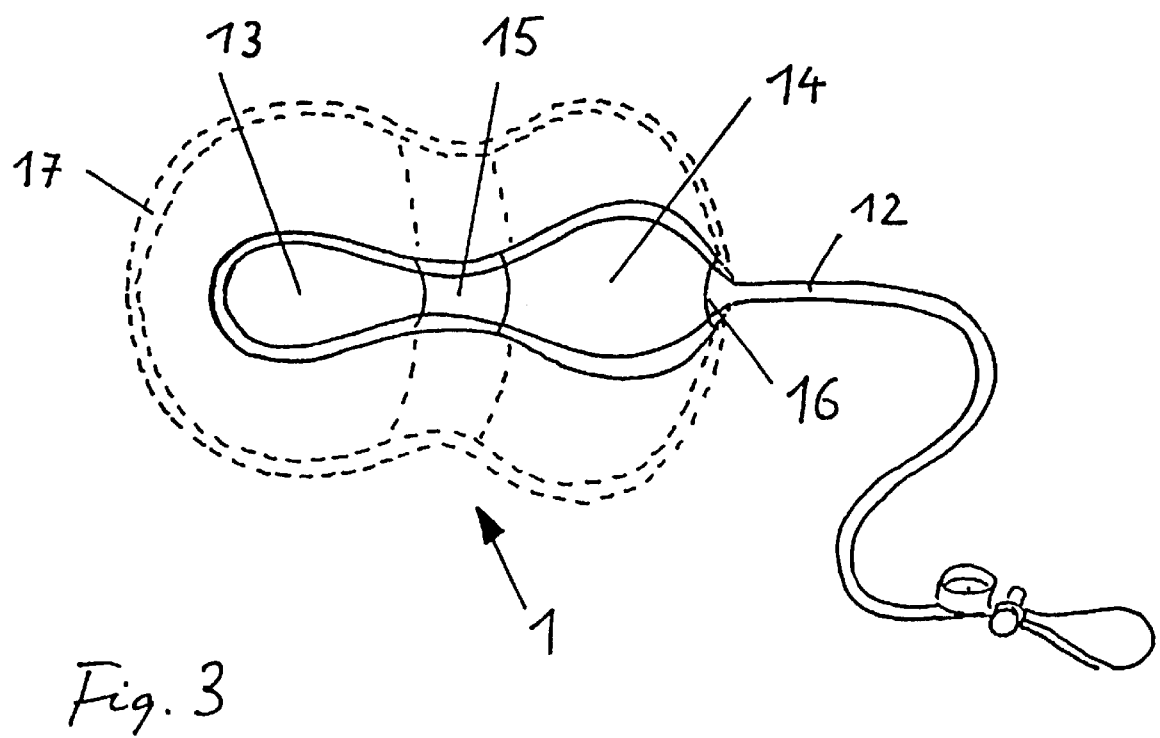
FIG. 3 illustrates a cross-section of the embodiment of the device according to FIGS. 1 and 2.

FIGS. 1 through 3 illustrate a balloon 1 for pneumatic dilation of the birth canal which is inserted into the vagina 2 towards the cervix 7 of uterus 10. The oval and FIG. 8 shaped expandable balloon 1 having a middle neck or waist portion 15 comprises, in its half 14 positioned exterior of the vagina 2, a greater wall strength than the half 13 positioned inside. The waist portion 15 of the balloon 1 itself is reinforced. The balloon 1 when deflated and folded up is inserted into the vagina 2 with lubricating gel such that approximately three to four centimeters of the balloon 1 can be seen in front of vulva 3. This is important since the outermost portion of the vagina 2 in particular, and above all, the vaginal orifice 4 should be expanded. This is the most sensitive part of the female birth canal and due to the danger of a tear of the perineum, it is at the same the most endagered anatomical part. The balloon 1 is now carefully pumped up using hand-pump 5 in steps of 20 mm Hg up to a maximum pressure of 160 mm Hg, which is monitored using manometer or pressure gauge 6. The stretching feeling subjectively experienced by the pregnant woman sets the limit for inflation. After approximately 15 to 20 minutes, the device 1 is carefully and gently pulled out in the direction of the vagina so that the patient experiences a "feeling of giving birth" and this sensation can be deepened in subsequent exercises which leads to a considerable tranquilizing effect. This exercise is repeated several times per day such that the patient expands the vaginal orifice continuously and completely painlessly. It is important that the desired diameter of the balloon is measured by corresponding pumping (i.e. by counting the pump strokes) outside of the vagina. The pressure on the pressure gauge should never exceed 200 mm Hg. The scale of the pressure gauge is correspondingly marked.

The maximum diameter of the waist portion should be 9.5 cm since the biparietal diameter of fetal cranium at birth is on average of this size, which corresponds to a cranial circumference of 35 cm. If an ultrasound examination carried out by the medical doctor determines that the child is particularly larger, the diameter of the expansion can be simply increased accordingly. However, the patient should still control the size of the balloon to suit her subjective feeling.

As a basis of measurement for the required birth dilation pressures, the following test results can be used:

According to scientific studies by R CALDEIRO-BARCIA the intraamnial pressure can rise under normal contraction activity up to 100 mm Hg. The systolic blood pressure of the mother (normally 120 mm Hg) can rise briefly during contractions during the period of expulsion up to between 180 to over 200 mm Hg. The pressure of the uterus musculature reaches, towards the end of the expansion during delivery, a pressure of up to 200 mm Hg against the surrounding vaginal tissue. According to C. LINDGREN, the maximum pressure on the fetal cranium in the area of the perineum 8 can reach a peak value up to 300 mm Hg during contractions shortly before birth. In order to keep the artificial dilation described herein within the physiological range, a limit of 200 mm Hg is recommended. Basically, the dilation should not be carried out before the 36th week of pregnancy.

The demonstration and explanation of the method for dilating the birth canal should basically be carried out with the patient by the physician in charge or by the midwife. It is recommended to carry out the first dilation under continuous CTG control (cardio topography=continuous recordal of fetal heart sounds and contractions) by the physician in charge or the midwife.

Cleaning of the device after use can be done with soap and water and air dried. Disinfecting using commercially available disinfectants is recommended.

FIG. 3 shows further the hose connection 16 as well as the expandable balloon 1 in its expanded state 17. The two parts or half-shells 13, 14 are glued or joined together overlapping about a circumferential seam which coincides with the waist portion 15. The overlapping region is shown in dashed lines.

Figure 4:
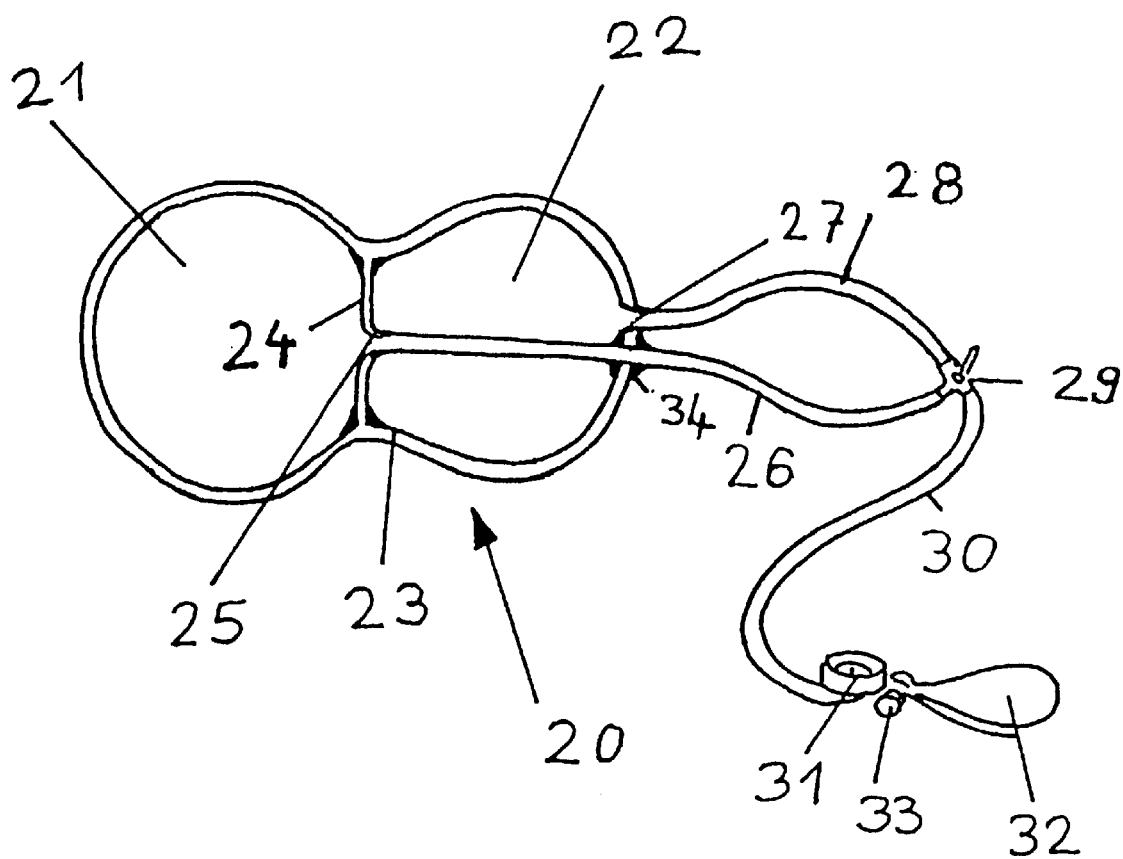
FIG. 4 shows a cross-section of a further embodiment of a device according to the present invention.

FIG. 4 shows a cross-section according to a further embodiment according to the present invention. The parts or half-shells 21, 22 and the balloon 20 are shown. In the area of the waist portion 23, a membrane 24 is arranged inside the balloon which membrane comprises an opening 25 which is connected to a first hose 26. The outer half-shell 22 is connected by means of a wall orifice 27 to a further connecting hose 28. The two connecting hoses 26, 28 are connected to a three-way valve 29 which in turn is connected by a hose 30 to a pressure gauge 21 and hand-pump 22. An air-release screw 33 is also provided between pressure gauge 31 and hand-pump 32 as well as an elastic seam 34 where the first connecting hose 26 passes through the wall of the outer half shell 22.

In the embodiment according to FIG. 4, three configurations can be selected using three-way valve 29. In the first configuration, a connection is established between hose 30 and both connecting hoses 26, 28. In this way, both chambers, i.e. both parts or half shells 21, 22 are simultaneously inflated or deflated. In the next configuration, a connection between hose 30 and connector hose 26 is established for the inner half-shell 21, whereby the connection to the second connector hose 28 is interrupted. In a third configuration, a connection is established between hose 30 and connector hose 28 to the outer half-shell 22 whereby the connection to the other connector hose 26 is interrupted. In this way, the outer half shell 22 can be inflated using the hand-pump 32 or deflated by means of the air-release screw 33. The connector hose 26 to the inner half shell 21 extends through the outer half-shell 22 directly to the membrane 24 where hose 26 connects to the opening 25 in membrane 24. As a result of such a twin-chamber construction, the volume of balloon 20 can be individually adjusted to the needs of the user. The pressure of each individually controlled balloon chambers can be separately monitored using pressure gauge 31.

What is claimed is:

1. An exercise method for preparing to give birth using a device for preparing to give birth, the device comprising:

an expandable elongated body which is positionable in the area of the vaginal orifice such that it is located partly inside the vagina in a vaginal interior and partly outside the vagina during use, the body is adapted to be expandable in its entirety, wherein the body further comprises a first expandable portion, a second expandable portion and a waist portion defined therebetween, said first expandable portion having an end that is adapted for insertion into the vaginal interior and that is uninterrupted by any portion of said device extending therethrough, said defined waist portion being expandable along with the remainder of the body, the waist portion being adapted to expand the vaginal orifice in preparation for giving birth, the waist portion being adopted to be self-centered in the area of the vaginal orifice during use, the waist portion being constricted with respect to the remainder of the body before insertion of the device through the vaginal orifice, during use of the device and after withdrawal of the device through the vaginal orifice, wherein said first expandable portion and said waist portion are configured to expand the vaginal interior and vaginal orifice respectively to mimic the extent of expansion that would occur while giving birth, and wherein said first expandable portion is positioned within said vaginal interior such that said first expandable portion does not contact the cervix during use, the exercise method comprising the steps of:

positioning the expandable body partly within the vaginal interior and partly outside and the vaginal orifice with the waist portion being self-centered in the area of the vaginal orifice, and thereafter expanding the expandable body to a desired dimension such that the waist portion is expanded to expand the vaginal orifice and said expandable body is expanded to expand said vaginal interior and without contacting the cervix, and maintaining the body in the expanded state for a predetermined time in its position.

2. Method according to claim 1, wherein the expansion of the expandable body is increased with repeated use in order to achieve an increasing preparatory stretching of the vaginal interior.

3. Method according to claim 2, wherein the expandable body is pulled from the vagina after a period of time.

4. Method according to claim 3, wherein the time period is between 10 to 20 minutes.

5. Method according to claim 3, wherein the expansion of the waist region is selected to be up to a diameter of 10 cm.

6. Device according to claim 5, characterized in that the outer and inner half-shells form two air tight chambers separated from one another.

7. Device according to claim 6, characterized in that the half-shell insertable in the vagina is inflatable by means of a separate inflation hose.

8. Device according to claim 6, characterized in that the device comprises a three-way valve for selecting the inflation mode of the outer and inner half-shells.

* * * * *